(12) United States Patent
Kono

(10) Patent No.: US 9,031,387 B2
(45) Date of Patent: May 12, 2015

(54) IMAGE PROCESSING APPARATUS

(75) Inventor: Takashi Kono, Hachioji (JP)

(73) Assignee: Olympus Corporation, Tokyo (JP)

( * ) Notice: Subject to any disclaimer, the term of this patent is extended or adjusted under 35 U.S.C. 154(b) by 914 days.

(21) Appl. No.: 12/857,892

(22) Filed: Aug. 17, 2010

(65) Prior Publication Data

US 2010/0310239 A1    Dec. 9, 2010

Related U.S. Application Data

(63) Continuation of application No. PCT/JP2008/071049, filed on Nov. 19, 2008.

(30) Foreign Application Priority Data

Feb. 19, 2008    (JP) ................................. 2008-038018

(51) Int. Cl.
| | | |
|---|---|---|
| H04N 5/783 | (2006.01) |
| A61B 1/04 | (2006.01) |
| A61B 1/00 | (2006.01) |
| G06T 7/20 | (2006.01) |

(52) U.S. Cl.
CPC .............. *A61B 1/041* (2013.01); *A61B 1/00009* (2013.01); *G06T 7/202* (2013.01); *G06T 2207/10068* (2013.01); *G06T 2207/30028* (2013.01)

(58) Field of Classification Search
USPC ........................................ 386/241, 248, 343
See application file for complete search history.

(56) References Cited

U.S. PATENT DOCUMENTS

| | | | | |
|---|---|---|---|---|
| 2001/0017887 A1* | 8/2001 | Furukawa et al. | ........ | 375/240.03 |
| 2007/0060798 A1* | 3/2007 | Krupnik et al. | ................ | 600/300 |
| 2007/0165950 A1* | 7/2007 | Nishida | .......................... | 382/177 |
| 2007/0195165 A1 | 8/2007 | Hirakawa | | |
| 2008/0119691 A1 | 5/2008 | Yagi et al. | | |
| 2008/0212881 A1* | 9/2008 | Hirakawa | ..................... | 382/224 |

FOREIGN PATENT DOCUMENTS

| | | |
|---|---|---|
| EP | 0 758 832 A2 | 9/1997 |
| JP | 2006-280792 | 10/2006 |
| WO | WO 01/87377 A2 | 11/2001 |
| WO | WO 2006/100808 A1 | 9/2006 |

OTHER PUBLICATIONS

English Translation of Japan Publication 2006-280792 Oct. 2006.*
International Search Report dated Jan. 20, 2009.
European Search Report dated Mar. 29, 2012 from corresponding European Patent Application No. EP 08 87 2675.7.
European Patent Convention Communication dated Mar. 12, 2015, from corresponding European Application No. 08 872 675.7.

* cited by examiner

*Primary Examiner* — Thai Tran
*Assistant Examiner* — William Tran
(74) *Attorney, Agent, or Firm* — Scully, Scott, Murphy & Presser, P.C.

(57) ABSTRACT

An image processing apparatus sequentially displays time-series images. The apparatus includes a movement-direction-change image extracting unit that detects a movement between images constituting the time-series images and extracts an image of which a movement direction is changed based on the detected movement between images; and a display speed controller that controls display speeds of the image extracted by the movement-direction-change image extracting unit and images adjacent to the image at a level relatively lower than display speeds of other images.

11 Claims, 17 Drawing Sheets

I(n-1)

I(n)

IMAGE PROCESSING APPARATUS

CROSS-REFERENCE TO RELATED APPLICATIONS

This application is a continuation of PCT international application Ser. No. PCT/JP2008/071049 filed on Nov. 19, 2008 which designates the United States, incorporated herein by reference, and which claims the benefit of priority from Japanese Patent Application No. 2008-038018, filed on Feb. 19, 2008, incorporated herein by reference.

BACKGROUND OF THE INVENTION

1. Field of the Invention

The present invention relates to an image processing apparatus that sequentially displays time-series images.

2. Description of the Related Art

In recent years, in the field of an endoscope, there has been proposed a swallowed capsule endoscope that has an imaging function for capturing an inside-subject image, a transmitting function for wirelessly transmitting image data captured by an imaging unit, and the like, which are accommodated in a capsule-shaped casing. Until the capsule endoscope is swallowed from the mouth of a patient who is a subject for examination to be introduced into the subject and is naturally discharged, the capsule endoscope moves inside an organ such as an esophagus, a stomach, a small intestine, or a large intestine inside the body in accordance with the peristalsis. Then, during moving inside the body, the capsule endoscope sequentially captures in-vivo images, for example, by two to four frames/sec and wirelessly transmits the captured image data to an external receiving apparatus. Inside-subject images, which are captured by the capsule endoscope and are received by the outside-body receiving apparatus, are sequentially displayed by a workstation for diagnosis or the like in time sequence and are confirmed by an observer such as a doctor.

A capsule endoscope captures a huge number of images. For this reason, a workstation for diagnosis detects the change between images on the basis of a degree of similarity between images that are located at the near positions in chronological order. The workstation lengthens a displaying time if the change is large and shortens a displaying time if the change is small. In this way, because the displaying time of each image is adjusted, the burden of an observer for the observation of an image is reduced. As this kind of technology, there has been known a technology for setting a plurality of pixel areas in an image and calculating the motion vector of each pixel area between time-series consecutive images to determine a degree of similarity between images. For example, there has been known a technique determining a degree of similarity between images in accordance with whether the directions of the obtained motion vectors accord with each other and skipping the display of images having a high degree of similarity or displaying images having a high degree of similarity at high speed (see Japanese Laid-open Patent Publication No. 2006-280792).

SUMMARY OF THE INVENTION

An image processing apparatus according to an aspect of the present invention is for sequentially displaying time-series images and includes a movement-direction-change image extracting unit that detects a movement between images constituting the time-series images and extracts an image of which a movement direction is changed based on the detected movement between images; and a display speed controller that controls display speeds of the image extracted by the movement-direction-change image extracting unit and images adjacent to the image at a level relatively lower than display speeds of other images.

A computer readable recording medium according to another aspect of the present invention includes programmed instructions. The instructions, when executed by a computer that includes a display unit for sequentially displaying time-series images, cause the computer to execute: detecting a movement between images constituting the time-series images; extracting an image of which a movement direction is changed based on the detected movement between images; and controlling display speeds of the extracted image and images adjacent to the extracted image at a level relatively lower than display speeds of other images.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
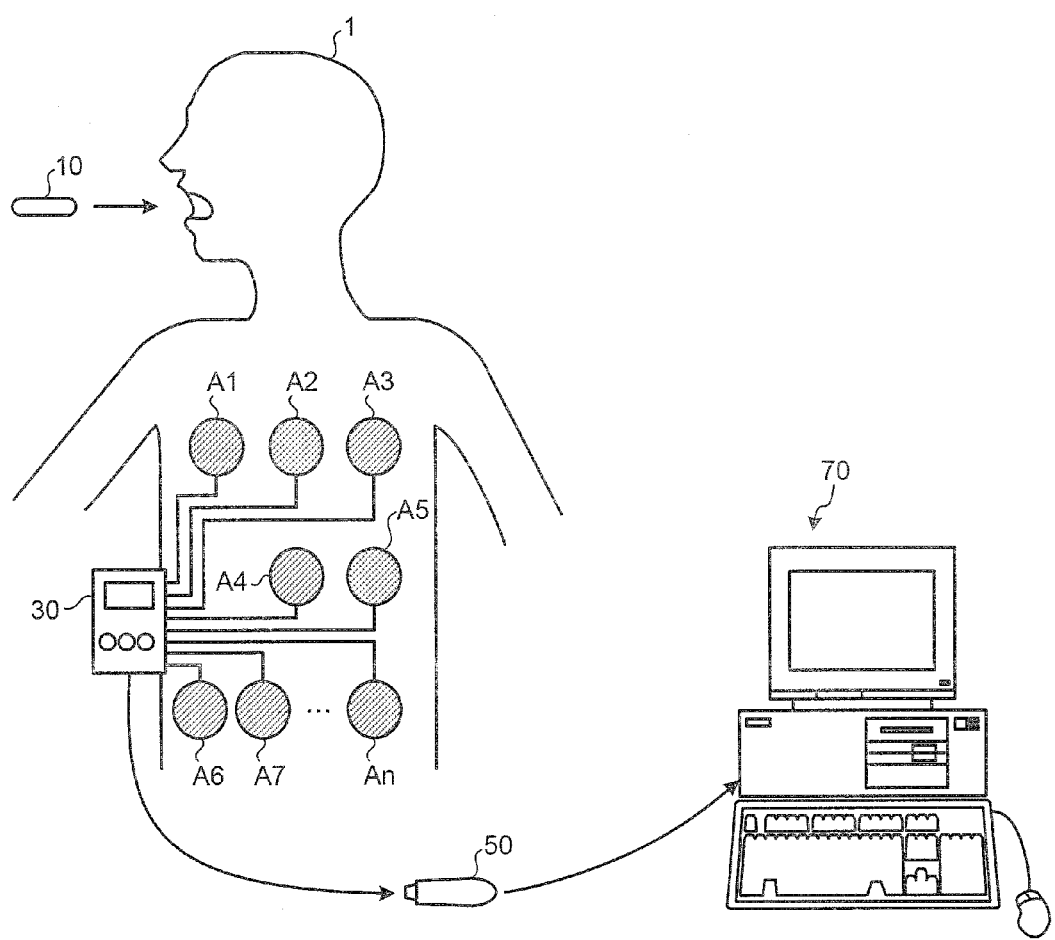
FIG. 1 is a schematic pattern diagram illustrating the entire configuration of an image processing system including an image processing apparatus according to a first embodiment.

Exemplary embodiments of the present invention will be explained below in detail with reference to the accompanying drawings. The present invention is not limited to the embodiments explained below. Moreover, in the drawings, the same components have the same reference numbers.

First Embodiment

FIG. 1 is a schematic pattern diagram illustrating the entire configuration of an image processing system including an image processing apparatus 70 according to a first embodiment. In the first embodiment, it will be explained about the case where time-series images captured by a capsule endoscope that moves inside a lumen in the body are processed and displayed. As illustrated in FIG. 1, the image processing system includes a capsule endoscope 10 that captures an image inside the lumen in the body of a subject 1, a receiving apparatus 30 that receives image data wirelessly transmitted from the capsule endoscope 10, the image processing apparatus 70 that performs image processing on the image received by the receiving apparatus 30, and the like. The transfer of image data between the receiving apparatus 30 and the image processing apparatus 70 is performed by, for example, a portable recording medium 50.

The capsule endoscope 10 has an imaging function, a radio function, an illuminating function for illuminating a portion to be captured, and the like, and is, for example, swallowed from the mouth of the subject 1 such as a person or an animal for examination and is introduced into the subject 1. Then, until it is naturally discharged, the capsule endoscope 10 sequentially captures internal images such as an esophagus, a stomach, a small intestine, or a large intestine at a predetermined capturing rate, and wirelessly transmits the captured images to the outside of the body. The contents of images captured by the capsule endoscope 10 include a mucous membrane, contents floating in a celomic cavity, foam, and the like, and further include an important part such as a lesioned part in some cases. Moreover, because the passage time of the capsule endoscope 10 inside the body is not constant, the time-series images having large change are continuously captured or the time-series images having similarity are continuously captured. In this case, an inside-lumen image captured by the capsule endoscope 10 is a color image having a pixel level (pixel value) for each color component of R (red), G (green), and B (blue) at each pixel position.

The receiving apparatus 30 includes a plurality of receiving antennas A1 to An, and receives image data wirelessly transmitted from the capsule endoscope 10 via the receiving antennas A1 to An. The receiving apparatus 30 is freely attached or detached with the portable recording medium 50, and sequentially saves the received image data in the portable recording medium 50. In this way, the receiving apparatus 30 accumulates images, indicating the inside of the subject 1, captured by the capsule endoscope 10 on the portable recording medium 50 in time sequence.

The receiving antennas A1 to An are configured with, for example, loop antennas, and are dispersed and arranged at predetermined positions on the surface of the body of the subject 1 as illustrated in FIG. 1. Specifically, for example, the receiving antennas are dispersed and arranged at positions on the surface of the body corresponding to the passage path of the capsule endoscope 10 inside the subject 1. Moreover, the receiving antennas A1 to An may be dispersed and arranged on a jacket worn by the subject 1. In this case, the receiving antennas A1 to An are arranged at predetermined positions on the surface of the body of the subject 1 corresponding to the passage path of the capsule endoscope 10 inside the subject 1 by wearing the jacket by the subject 1. Moreover, the receiving antennas are arranged more than one for the subject 1, and the number of antennas is not limited.

The image processing apparatus 70 is realized by a general-purpose computer such as a workstation or a personal computer, and is freely attached or detached with the portable recording medium 50. The image processing apparatus 70 acquires the time-series images that are saved in the portable recording medium 50, and sequentially displays the acquired time-series images on a display such as LCD or ELD.

Figure 2:
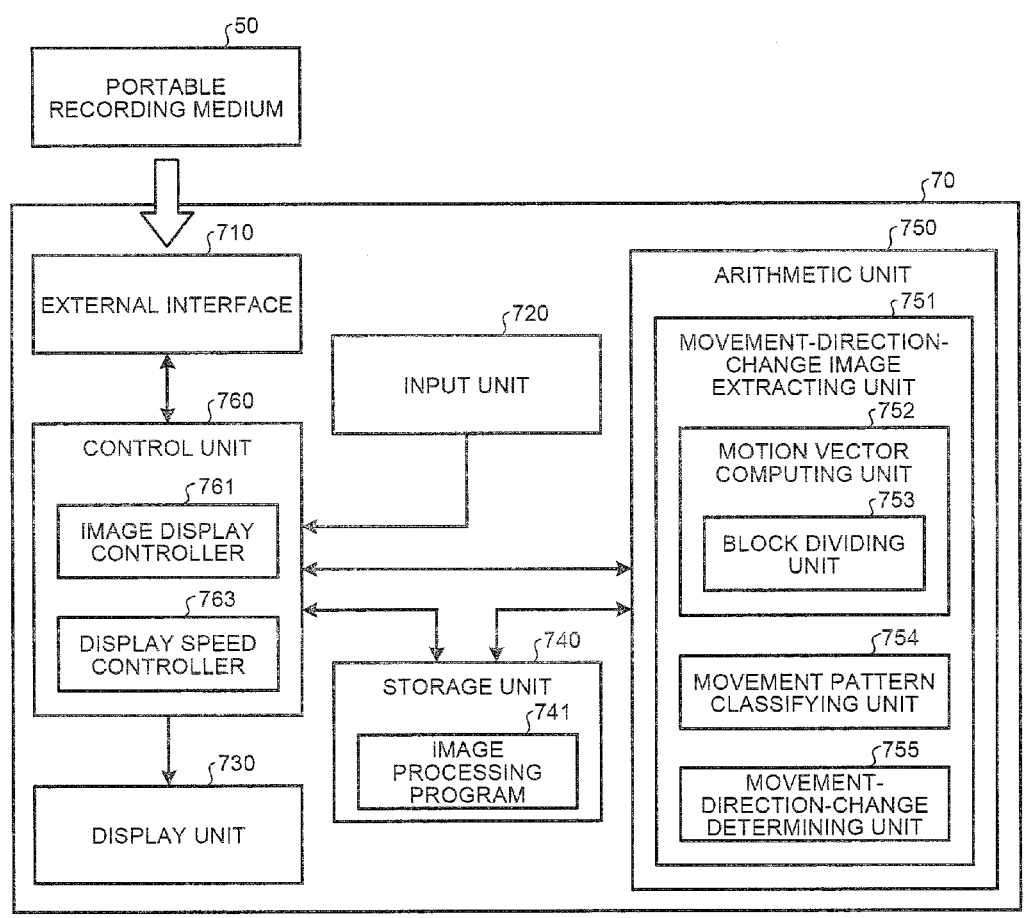
FIG. 2 is a block diagram explaining the functional configuration of the image processing apparatus according to the first embodiment.

FIG. 2 is a block diagram explaining the functional configuration of the image processing apparatus 70 according to the first embodiment. In the first embodiment, the image processing apparatus 70 includes an external interface 710, an input unit 720, a display unit 730, a storage unit 740, an arithmetic unit 750, and a control unit 760 that controls all the operations of the image processing apparatus 70.

The external interface 710 acquires the image data of time-series images that are captured by the capsule endoscope 10 and are received by the receiving apparatus 30. For example, the external interface 710 is configured with a reader device that removably mounts thereon the portable recording medium 50 and reads out the image data saved in the portable recording medium 50. The image data of time-series images read by the external interface 710 are maintained in the storage unit 740, are processed by the arithmetic unit 750, and are sequentially displayed on the display unit 730 under the control of the control unit 760. It should be noted that the acquisition of time-series images captured by the capsule endoscope 10 is not limited to a configuration of using the portable recording medium 50. For example, the present invention may have a configuration that a separate server is provided instead of the portable recording medium 50 and time-series images are previously saved in the server. In this case, the image processing apparatus includes a communication device or the like that connects the external interface with the server. The image processing apparatus may perform data communication with the server via the external interface to acquire the time-series images. Alternatively, the present invention may have a configuration that the image processing apparatus previously saves the time-series images captured by the capsule endoscope 10 in the storage unit 740 and reads out the images from the storage unit 740 to acquire the time-series images.

The input unit 720 is realized by, for example, a keyboard, a mouse, a touch panel, various types of switches, and the like, and outputs the input instruction information to the control unit 760. The display unit 730 is realized by a display device such as LCD or ELD, and displays various types of screens including the display screen of time-series images under of the control of the control unit 760.

The storage unit 740 is realized by various types of IC memories such as ROM or RAM that is an updatable flash memory, an information storage medium such as a hard disk or CD-ROM that is built in or connected by a data communication terminal, a reader therefor, and the like. The storage unit 740 stores a program related to the operations of the image processing apparatus 70, a program for realizing various functions of the image processing apparatus 70, data related to the execution of the programs, and the like. Furthermore, the storage unit 740 stores an image processing program 741 for processing the time-series images to make the display unit 730 sequentially display the images.

The arithmetic unit 750 processes the time-series images captured by the capsule endoscope 10 and performs various arithmetic processing for detecting the change of a movement direction between consecutive images. The arithmetic unit 750 includes a movement-direction-change image extracting unit 751 that functions as a movement-direction-change image extracting means that detects a movement between consecutive images and extracts an image (hereinafter, "movement-direction-change image") of which the movement direction is changed. The movement-direction-change image extracting unit 751 includes a motion vector computing unit 752 that functions as a motion vector computing means that computes a motion vector between images every block, a movement pattern classifying unit 754 that functions as a movement pattern determining means that classifies movement patterns in accordance with the direction of a motion vector between images, and a movement-direction-change determining unit 755 that determines the change of a movement direction between images. Moreover, the motion vector computing unit 752 includes a block dividing unit 753 that functions as a block dividing means that divides an image into a plurality of blocks (area division).

The control unit 760 is realized by hardware such as CPU. The control unit 760 performs the transfer of an instruction and data to each unit constituting the image processing apparatus 70 and overall controls all the operations of the image processing apparatus 70, on the basis of the image data of time-series images acquired via the external interface 710, a manipulated signal input from the input unit 720, a program and data stored in the storage unit 740, and the like. Moreover, the control unit 760 includes an image display controller 761 that performs a control to sequentially display images constituting time-series images on the display unit 730 and a display speed controller 763 that functions as a display speed control means that controls the display speeds of a movement-direction-change image extracted by the movement-direction-change image extracting unit 751 of the arithmetic unit 750 and images adjacent to the image relatively lower than the display speeds of the other images.

Next, it will be explained about a processing procedure performed by the image processing apparatus 70 according to the first embodiment with reference to a flowchart illustrated in FIG. 3. A process explained in this case is realized by the operations of the units of the image processing apparatus 70 in accordance with the image processing program 741 stored in the storage unit 740.

Figure 3:
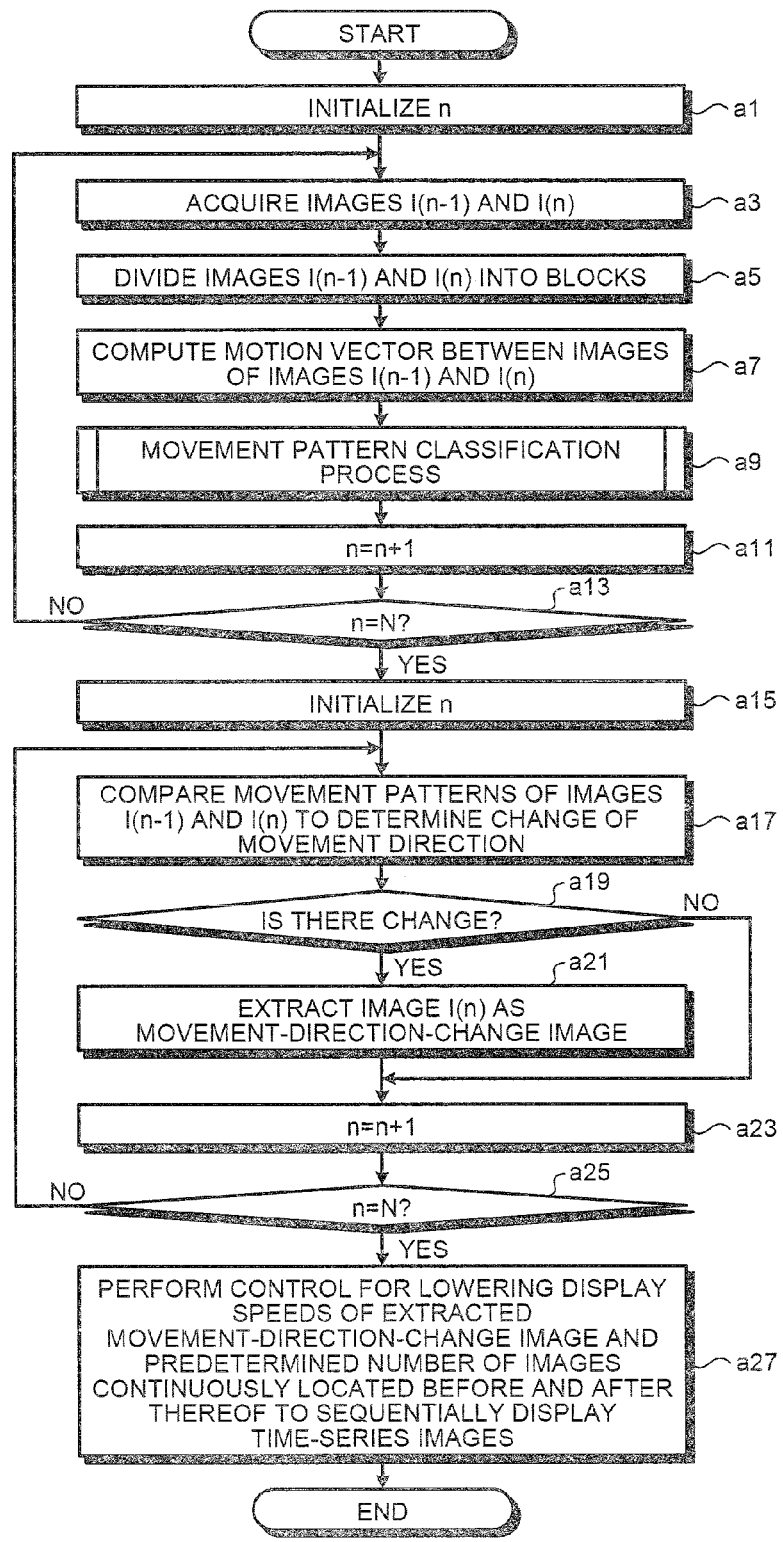
FIG. 3 is a flowchart illustrating a processing procedure performed by the image processing apparatus according to the first embodiment.

As illustrated in FIG. 3, in the image processing apparatus 70 according to the first embodiment, the arithmetic unit 750 first initializes an image number "n" for identifying the time-series sequence of an image that is a processing target (Step a1). Then, the arithmetic unit 750 acquires an image I(n−1) of an image number "n−1" and an image I(n) of the image number "n" from the time-series images that are acquired via the external interface 710 and is stored in the storage unit 740 (Step a3).

Next, the block dividing unit 753 divides a pixel space of each image data of the images I(n−1) and I(n) into a plurality of blocks (pixel areas) (Step a5). The size of the block and the number of the blocks may be previously set, or may be changed by the operation of a user. By dividing a space into blocks, the blocks are equally arranged on the pixel space. For example, a pixel space of each image data of the images I(n−1) and I(n) is divided into 16 (4×4) blocks.

Figure 4:
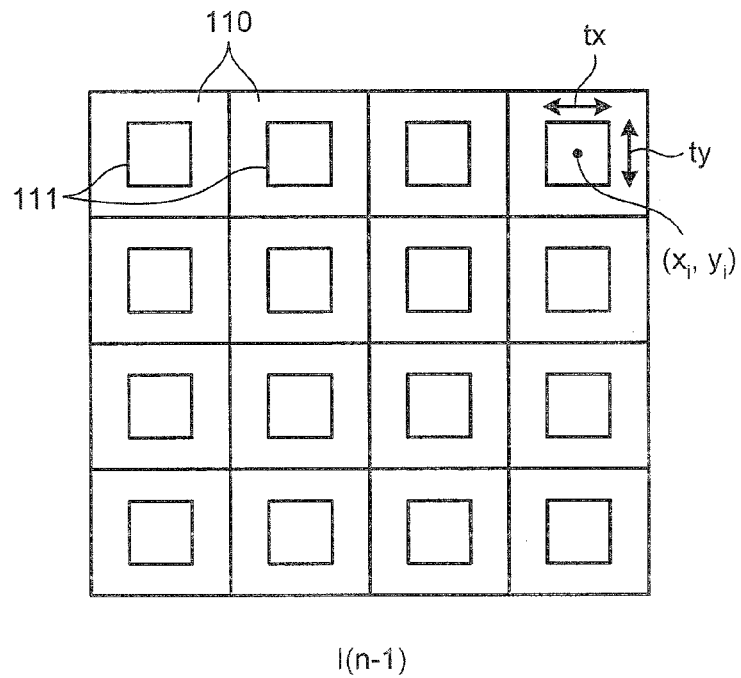
FIG. 4 is a diagram explaining a computation method of a motion vector.
Figure 5:
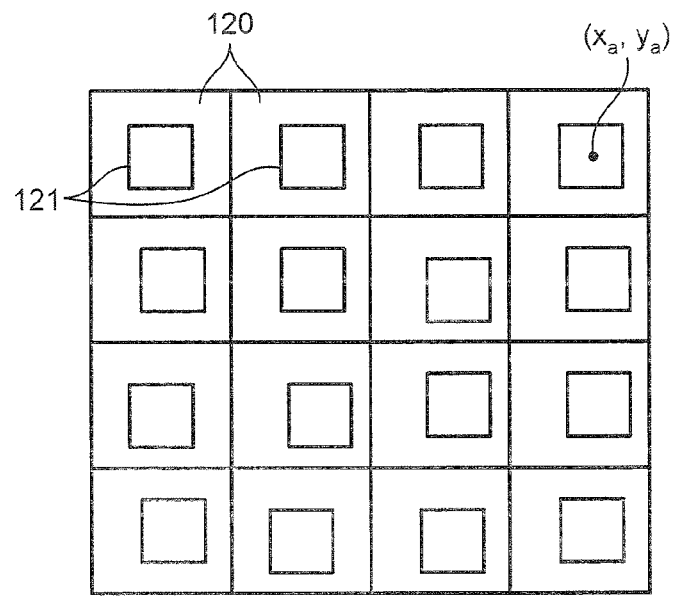
FIG. 5 is a diagram explaining a computation method of a motion vector.

Next, the motion vector computing unit 752 computes a motion vector between the images I(n−1) and I(n) for each the corresponding block (Step a7). For example, the motion vector computing unit 752 computes a motion vector by using the normalized cross-correlation of the G components of the images I(n−1) and I(n). The reason of using a G component is that the sensitivity of a G component among RGB components is the most and the difference of a brightness component is easy to occur. FIGS. 4 and 5 are diagrams explaining the computation method of a motion vector. FIG. 4 illustrates a pixel space of the image I(n−1) and FIG. 5 illustrates a pixel space of the image I(n). In this case, the pixel space of the image I(n−1) of FIG. 4 is divided into 16 blocks 110 by using the process of Step a5 illustrated in FIG. 3. Similarly, the pixel space of the image I(n) illustrated in FIG. 5 is divided into 16 blocks 120. In the case of the computation of a motion vector, the motion vector computing unit 752 associates template areas 111 in the image I(n−1) with matching areas 121 in the image I(n) in units of block.

In other words, as illustrated in FIG. 4, the motion vector computing unit 752 first sets the template areas 111 in the blocks 110 of the image I(n−1). For example, an area of which the center is central coordinates ($x_i$, $y_i$ and the size is a size (tx, ty) smaller than each the block 110 is set in the center of each the block 110 as the template area 111. The "i" is a template area number. In this case, because the number of the blocks 110 is 16, i=1 to 16.

Figure 6:
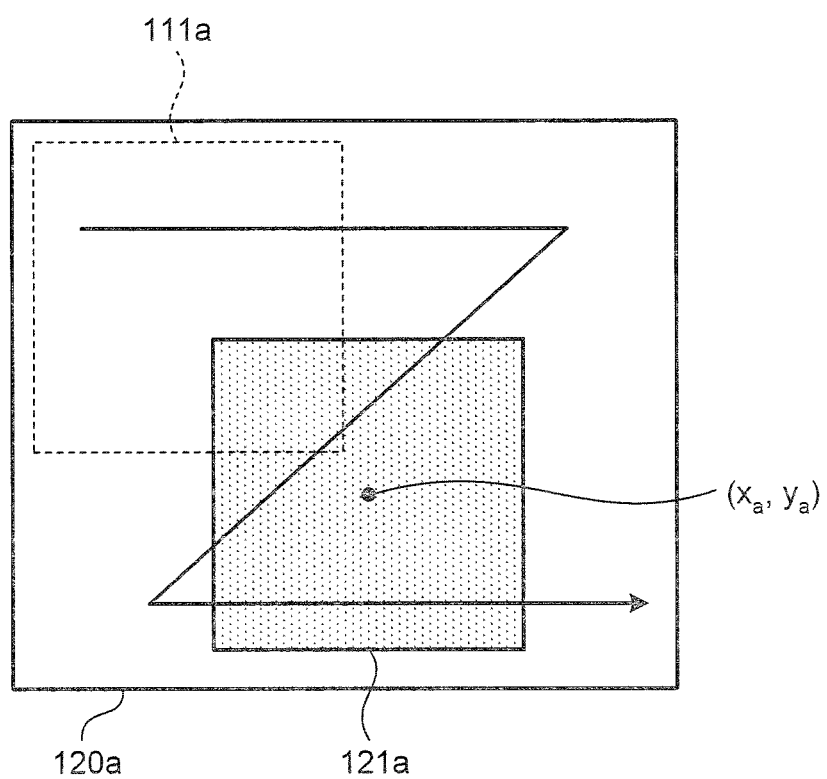
FIG. 6 is a diagram explaining matching.

Next, the motion vector computing unit 752 performs matching by normalized cross-correlation on the corresponding block 120 of the image I(n) by using the pixel data of the template area 111 of each the block 110 of the image I(n−1). FIG. 6 is a diagram explaining matching and illustrates an example of detecting a matching area 121a in the corresponding block 120a of the image I(n) by using the pixel data of a template area 111a. In the matching, an area most similar to the template area 111a is searched from the block 120a and the normalized cross-correlation value is calculated. Then, an area that is most matched with the template area 111a, that is to say, that has a high normalized cross-correlation value is detected as the matching area 121a. In this case, the central coordinates of the detected matching area 121a is ($x_a$, $y_a$). The "a" is a matching area number. Because the number of the blocks 120a is 16, a=1 to 16.

More specifically, the motion vector computing unit 752 performs matching by using the variance value of the G component of the template area and the matching area, and computes a normalization cross-correlation value E in accordance with the following Equation (1). The function f(n, x, y) is the image data of the image number "n".

$$E = \frac{\sum_{q=-\frac{ty}{2}}^{\frac{ty}{2}} \sum_{p=-\frac{tx}{2}}^{\frac{tx}{2}} (f(n-1, xi+p, yi+q) - \overline{f}(n-1))(f(n, xa+p, ya+q) - \overline{f}(n))}{\sqrt{\sum_{q=-\frac{ty}{2}}^{\frac{ty}{2}} \sum_{p=-\frac{tx}{2}}^{\frac{tx}{2}} (f(n-1, xi+p, yi+q) - \overline{f}(n-1))^2} \sqrt{\sum_{q=-\frac{ty}{2}}^{\frac{ty}{2}} \sum_{p=-\frac{tx}{2}}^{\frac{tx}{2}} (f(n, xa+p, ya+q) - \overline{f}(n))^2}} \quad (1)$$

In this way, as illustrated in FIG. 5, the motion vector computing unit 752 performs matching on each of the blocks 120 and detects the matching area 121.

Then, the motion vector computing unit 752 computes the change of central coordinates $(x_i, y_i)$ and $(x_a, y_a)$ as a motion vector between the template area 111 of each the block 110 of the image I(n−1) and the matching area 121 of the corresponding block 120 of the image I(n). The obtained matching result data is maintained in the storage unit 740. Specifically, the central coordinates of the obtained matching area, the normalized cross-correlation value E, the motion vector, and the like are stored in association with each template area number.

Figure 7:
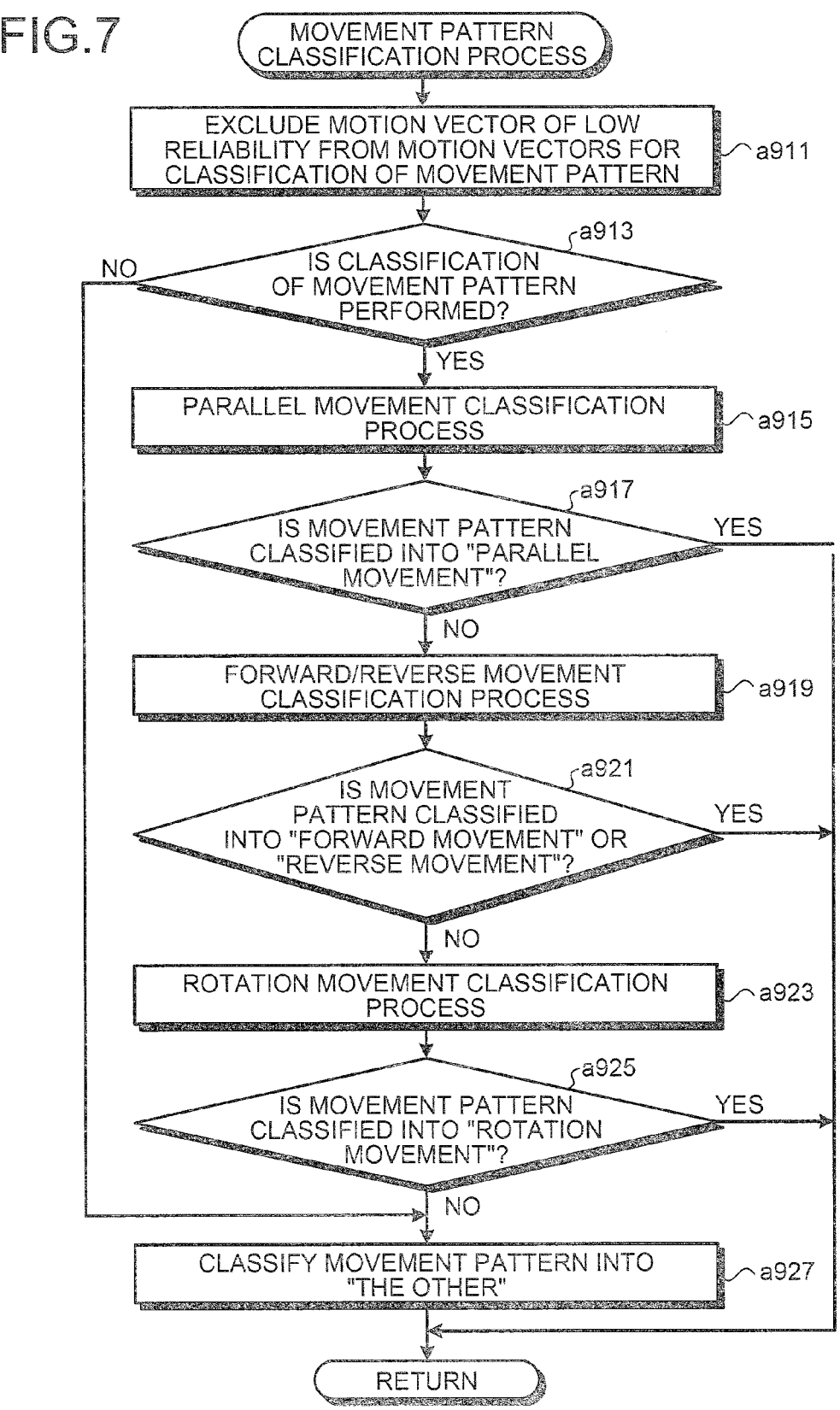
FIG. 7 is a flowchart illustrating the detailed processing procedure of a movement pattern classification process.

After the motion vector is computed, as illustrated in FIG. 3, the movement pattern classifying unit 754 executes a movement pattern classification process to classify the movement pattern of the image I(n) (Step a9). The classification of the movement pattern of the image I(n) is performed by classifying a movement pattern to one of "parallel movement upper", "parallel movement upper-left", "parallel movement left", "parallel movement lower-left", "parallel movement lower", "parallel movement lower-right", "parallel movement right", "parallel movement upper-right", "forward movement", "reverse movement", "left-rotation movement", "right-rotation movement", and "the other", on the basis of a motion vector between the images I(n−1) and I(n). FIG. 7 is a flowchart illustrating the detailed processing procedure of a movement pattern classification process.

In other words, the movement pattern classifying unit 754 first defines the normalized cross-correlation value E obtained as the result of matching performed at Step a7 of FIG. 3 as the reliability of a motion vector between the images I(n−1) and I(n). When the reliability of a motion vector is low, the movement pattern classifying unit 754 performs a process for excluding the motion vector from motion vectors for the classification of a movement pattern as the failure of matching (Step a911). Next, the movement pattern classifying unit 754 determines whether the classification of a movement pattern is performed. For example, when the number of motion vectors that can be used for the classification of a movement pattern is less than or equal to the half of the total number of motion vectors (less than or equal to eight in the first embodiment) by excluding motion vectors having a low reliability, the movement pattern classifying unit 754 determines that the classification of a movement pattern is not performed (Step a913: No) and moves the process control to Step a927 to classify the movement pattern of the image I(n) into "the other". This reason is that the number of the failures of matching is large and thus a result does not have reliability even if the classification of a movement pattern is performed.

Figure 8:
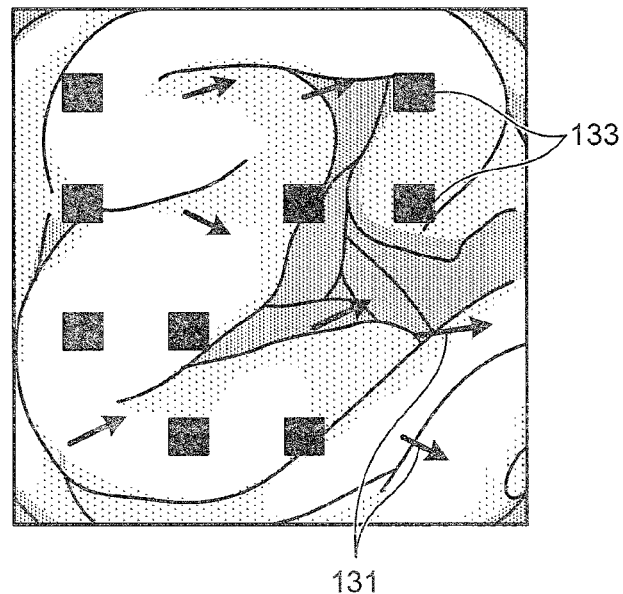
FIG. 8 is a diagram illustrating an example of an image I(n)

FIG. 8 is a diagram illustrating an example of the image I(n). In FIG. 8, motion vectors 131 that can be used for the classification of a movement pattern set between the images I(n−1) and I(n) are illustrated. For example, when the captured position of the capsule endoscope 10 is largely changed before and after time series and thus the vision of an image is largely changed, the normalized cross-correlation value E obtained as the result of matching becomes low. For this reason, as in the image I(n) illustrated by FIG. 8, many parts 133 of which the reliability of a motion vector is low occur. In such a case, the movement pattern is classified into "the other". It is assumed that the movement pattern is classified into "the other" when the number of motion vectors that can be used for the classification of a movement pattern is not more than half. However, the number is not limited to half or less. A threshold value may be appropriately set.

On the other hand, when the classification of a movement pattern is performed (Step a913: Yes), the movement pattern classifying unit 754 performs a process (parallel movement classification process) for classifying the movement pattern of the image I(n) into "parallel movement" (Step a915). When a movement pattern is "parallel movement", all the motion vectors between the images I(n−1) and I(n) have the same direction. For this reason, when the directions of motion vectors faces substantially the same direction, the movement pattern classifying unit 754 classifies the movement pattern of the image I(n) into "parallel movement". Specifically, the movement pattern classifying unit 754 calculates the variance of the directions of motion vectors, and classifies a movement pattern into "parallel movement" when the value of the obtained variance is smaller than a predetermined threshold value.

Figure 9:
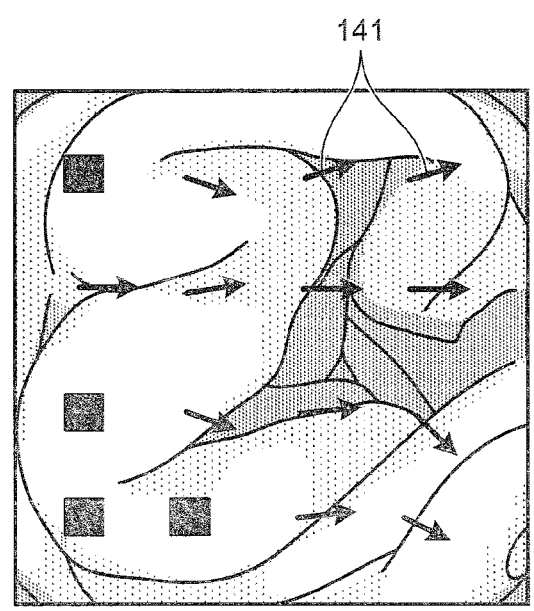
FIG. 9 is a diagram illustrating an example of the image I(n)

FIG. 9 is a diagram illustrating an example of the image I(n). In FIG. 9, motion vectors 141 that can be used for the classification of a movement pattern set between the images I(n−1) and I(n) are illustrated. As in the image I(n) illustrated by FIG. 9, when the motion vectors 141 face substantially the same direction, a movement pattern is classified into "parallel movement". When the movement pattern is classified into "parallel movement", the movement pattern classifying unit 754 subsequently calculates the average of the directions of the motion vectors, and classifies the movement pattern into one of "upper", "upper-left", "left", "lower-left", "lower", "lower-right", "right", and "upper-right". In this way, the movement pattern of the image I(n) classified into "parallel movement" is further classified into one of "parallel movement upper", "parallel movement upper-left", "parallel movement left", "parallel movement lower-left", "parallel movement lower", "parallel movement lower-right", "parallel movement right", and "parallel movement upper-right", of which moving directions are different.

Next, as illustrated in FIG. 7, the movement pattern classifying unit 754 determines whether the movement pattern of the image I(n) is classified into "parallel movement", and terminates the process and returns the process control to Step a9 of FIG. 3 when the movement pattern is classified (Step a917: Yes). On the other hand, when the movement pattern is not classified (Step a917: No), the movement pattern classifying unit 754 performs a process (forward/reverse movement classification process) for classifying the movement pattern of the image I(n) into "forward movement" or "reverse movement" (Step a919).

Figure 10:
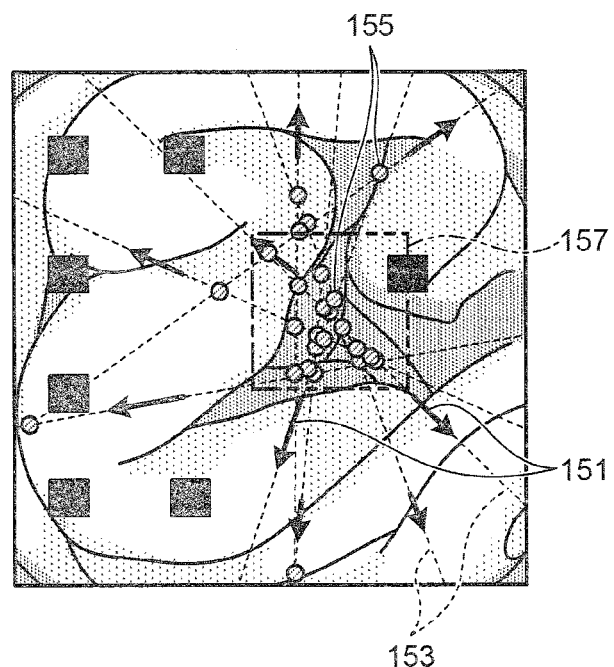
FIG. 10 is a diagram illustrating an example of the image I(n)

FIG. 10 is a diagram illustrating an example of the image I(n). In FIG. 10, motion vectors 151 that can be used for the classification of a movement pattern set between the images I(n−1) and I(n) are illustrated. In the case of the classification of "forward movement" or "reverse movement", the movement pattern classifying unit 754 sets straight lines 153 along the motion vectors 151 and sets voting points 155 at positions at which the set straight lines 153 intersect with each other, as shown by a broken line of FIG. 10. Then, when the set voting points 155 are, for example, concentrated in the coordinate range of a preset predetermined size, the movement pattern classifying unit 754 classifies a movement pattern into "forward movement" or "reverse movement". For example, the movement pattern classifying unit 754 scans on the image I(n) to search a coordinate range 157 in which voting points not less than the predetermined number of reference voting points are included. When the coordinate range is searched, the movement pattern classifying unit 754 classifies a move-ment pattern into "forward movement" or "reverse movement". The number of reference voting points can be appropriately set to, for example, not less than the half of the total number of voting points.

Then, when a movement pattern is classified into "forward movement" or "reverse movement", the movement pattern classifying unit 754 classifies a movement pattern into "forward movement" if the direction of each motion vector faces the direction of an average position of the voting points within the searched coordinate range. On the other hand, the movement pattern classifying unit 754 classifies a movement pattern into "reverse movement" if the direction of each motion vector faces the opposite direction. For example, in the example of FIG. 10, because each of the motion vectors 151 faces a direction opposite to the coordinate range 157 on which the voting points 155 are concentrated, the movement pattern is classified into "reverse movement". Moreover, when the mucous membrane of an alimentary lumen shrinks due to a peristalsis and thus images are obtained in a manner such that the capsule endoscope 10 moves forward or reversely even if the position of the capsule endoscope 10 does not move actually, the movement pattern is classified into "forward movement" or "reverse movement".

Next, as illustrated in FIG. 7, the movement pattern classifying unit 754 determines whether the movement pattern of the image I(n) is classified into "forward movement" or "reverse movement". When the movement pattern is classified (Step a921: Yes), the movement pattern classifying unit 754 terminates the process and returns the process control to Step a9 of FIG. 3. On the other hand, when the movement pattern is not classified (Step a921: No), the movement pattern classifying unit 754 performs a process (rotation movement classification process) for classifying the movement pattern of the image I(n) into "rotation movement" (Step a923).

Figure 11:
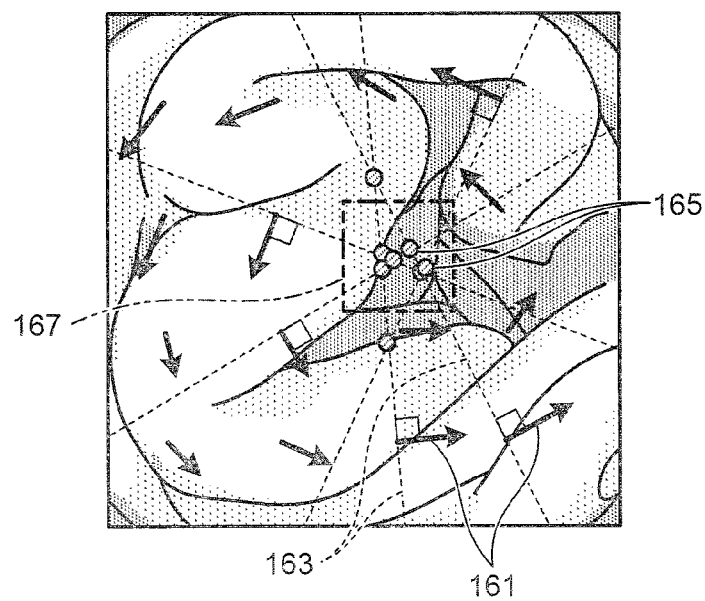
FIG. 11 is a diagram illustrating an example of the image I(n)

FIG. 11 is a diagram illustrating an example of the image I(n). In FIG. 11, motion vectors 161 that can be used for the classification of a movement pattern set between the images I(n−1) and I(n) are illustrated. In the case of the classification of "rotation movement", the movement pattern classifying unit 754 sets straight lines 163 perpendicular to the motion vectors 161 and sets voting points 165 at positions at which the set straight lines 163 intersect with each other, as shown by a broken line of FIG. 11. Then, when the set voting points 165 are, for example, concentrated in the coordinate range of a preset predetermined size, the movement pattern classifying unit 754 classifies a movement pattern into "rotation movement". For example, the movement pattern classifying unit 754 scans on the image I(n) to search a coordinate range 167 in which voting points not less than the predetermined number of reference voting points are included. When the coordinate range is searched, the movement pattern is classified into "rotation movement". The number of reference voting points can be appropriately set to, for example, not less than the half of the total number of voting points.

Figure 12:
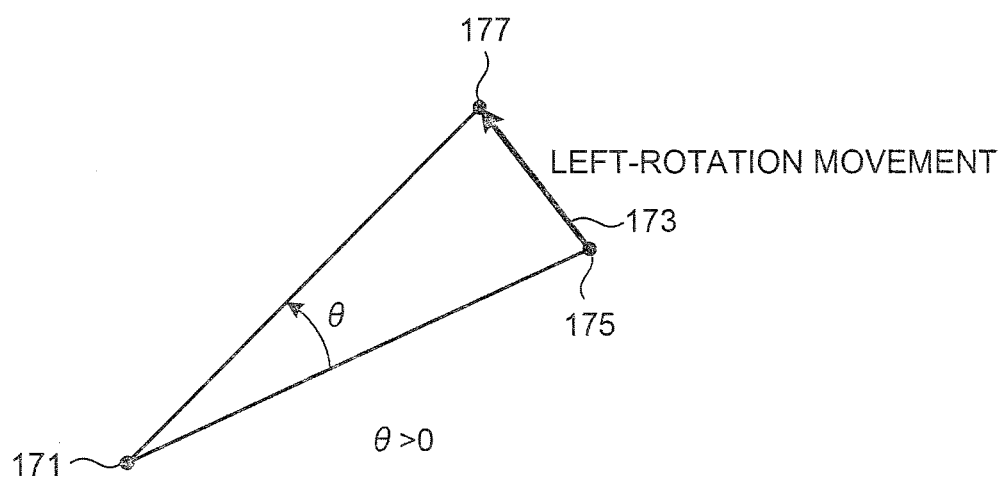
FIG. 12 is a diagram explaining the determination method of a rotation direction.
Figure 13:
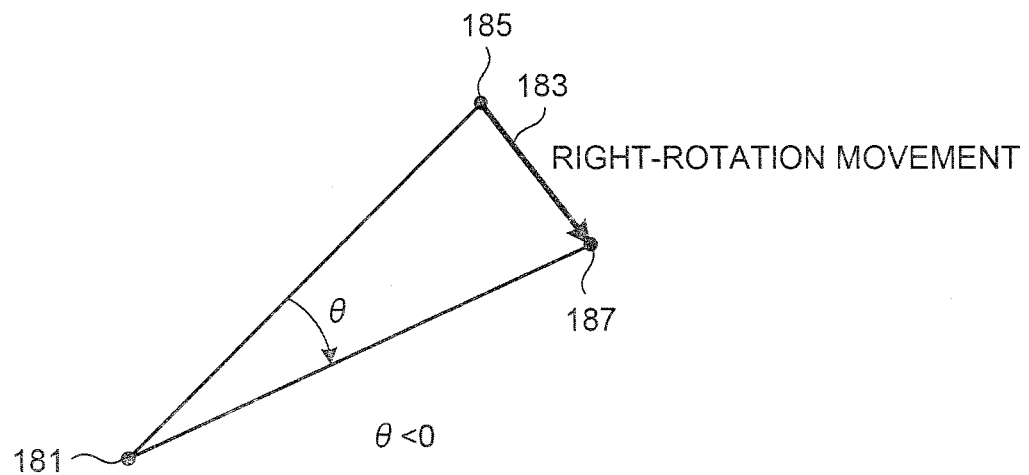
FIG. 13 is a diagram explaining the determination method of a rotation direction.

Then, when the movement pattern is classified into "rotation movement", the movement pattern classifying unit 754 subsequently defines the average position of voting points within the searched coordinate range as a rotational center position. Then, the movement pattern classifying unit 754 computes an angle formed by straight lines, which connect the starting point and ending point with the rotational center position, for each motion vector, and classifies a rotation direction into one of "left" and "right" in accordance with whether the obtained angle is a positive value or not a negative value. FIGS. 12 and 13 are diagrams explaining the determination method of a rotation direction. As illustrated in FIG. 12, when an angle, which is formed by a straight line that connects a rotational center position 171 with a starting point 175 of a motion vector 173 and a straight line that connects the rotational center position 171 with an ending point 177 of the motion vector 173, is a positive value, a rotation direction is defined as "left". On the other hand, as illustrated in FIG. 13, when an angle, which is formed by a straight line that connects a rotational center position 181 with a starting point 185 of a motion vector 183 and a straight line that connects the rotational center position 181 with an ending point 187 of the motion vector 183, is a negative value, a rotation direction is defined as "right". In this way, the movement pattern of the image I(n) classified into "rotation movement" is further classified into one of "left-rotation movement" and "right-rotation movement" of which the rotation directions are different.

Then, as illustrated in FIG. 7, the movement pattern classifying unit 754 determines whether the movement pattern of the image I(n) is classified into "rotation movement". When the movement pattern is classified (Step a925: Yes), the movement pattern classifying unit 754 terminates the process and returns the process control to Step a9 of FIG. 3. On the other hand, when the movement pattern is not classified (Step a925: No), the movement pattern classifying unit 754 moves the process control to Step a927 to classify the movement pattern of the image I(n) into "the other". In other words, when the directions of motion vectors in the image I(n) do not have regularity and the movement pattern between the images I(n−1) and I(n) is classified into any one of "parallel movement", "forward movement", "reverse movement", and "rotation movement", the movement pattern classifying unit 754 classifies the movement pattern of the image I(n) into "the other" at Step a927 and returns the process control to Step a9 of FIG. 3. The movement pattern of the image I(n) classified by the movement pattern classification process is maintained in the storage unit 740.

As illustrated in FIG. 3, after the movement pattern classification process is executed, the arithmetic unit 750 increments the image number n to be n=n+1 (Step a11), and determines the presence or absence of an image that is next processed in accordance with whether the value of "n" is identical with the total number "N" of images constituting time-series images. If it is not n=N (Step a13: No), the process control is returned to Step a3. On the other hand, when it is n=N (Step a13: Yes), the arithmetic unit 750 again initializes the image number "n" (Step a15). Then, the movement-direction-change determining unit 755 reads out and acquires the movement patterns of the images I(n−1) and I(n) from the storage unit 740. Then, the movement-direction-change determining unit 755 compares the acquired movement patterns and determines the change of a movement direction (Step a17). When the movement direction is not changed (Step a19: No), the process control moves to Step a23.

On the other hand, when the movement direction is changed (Step a19: Yes), the movement-direction-change image extracting unit 751 extracts the image I(n) as a movement-direction-change image (Step a21) and moves the process control to Step a23. Specifically, the movement-direction-change determining unit 755 determines the degree of similarity when the movement patterns of the images I(n−1) and I(n) are different. Then, the movement-direction-change determining unit 755 determines that the movement direction is not changed when the movement patterns are similar and determines that the movement direction is changed when the movement patterns are not similar. For example, "parallel movement upper" and "parallel movement upper-left", "parallel movement upper-left" and "parallel movement left", "parallel movement left" and "parallel movement lower-left", "parallel movement lower-left" and "parallel movement lower", "parallel movement lower" and "parallel movement lower-right", "parallel movement lower-right" and "parallel movement right", "parallel movement right" and "parallel movement upper-right", and "parallel movement upper-right" and "parallel movement upper" are predefined as similar movement patterns. When a combination of movement patterns of the images I(n−1) and I(n) accords with any of similar movement patterns, the movement-direction-change determining unit 755 determines that the movement direction is not changed. The extracted movement-direction-change image data (image number) is maintained in the storage unit 740.

Then, at Step a23, the arithmetic unit 750 increments the image number "n" to be n=n+1, and then determines the presence or absence of an image that is the next processing target in accordance with whether the value of "n" is identical with the total number "N" of images constituting time-series images. If it is not n=N (Step a25: No), the process control is returned to Step a17. On the other hand, when it is n=N (Step a25: Yes), the image display controller 761 subsequently performs a control for sequentially displaying images that constitute time-series images in time sequence. At this time, the display speed controller 763 defines a predetermined number of images, which are continuously located before and after the movement-direction-change image extracted at Step a21, as adjacent images, and performs a control for lowering the display speeds of the movement-direction-change image and the adjacent images relatively compared to the display speeds of the other images (Step a27).

As described above, according to the first embodiment, the image processing apparatus can classify the movement pattern of each image on the basis of a motion vector between images constituting time-series images and extract an image of which the movement direction is changed on the basis of the movement pattern. Then, when sequentially displaying the time-series images, because the image processing apparatus can perform a control for lowering the display speeds of the image of which the movement direction is changed and the images adjacent to the image relatively compared to the display speeds of the other images, an observer can observe an image of which the movement direction is changed at a slower display speed than that of the other images when observing the time-series images. Moreover, when the display speed becomes slow at the time of observation, an observer can predict that the movement direction of an image is changed. According to this, the image processing apparatus can prevent an observer from missing display contents. Therefore, the contents of time-series images can be efficiently grasped and thus observation efficiency can be improved.

Figure 14:
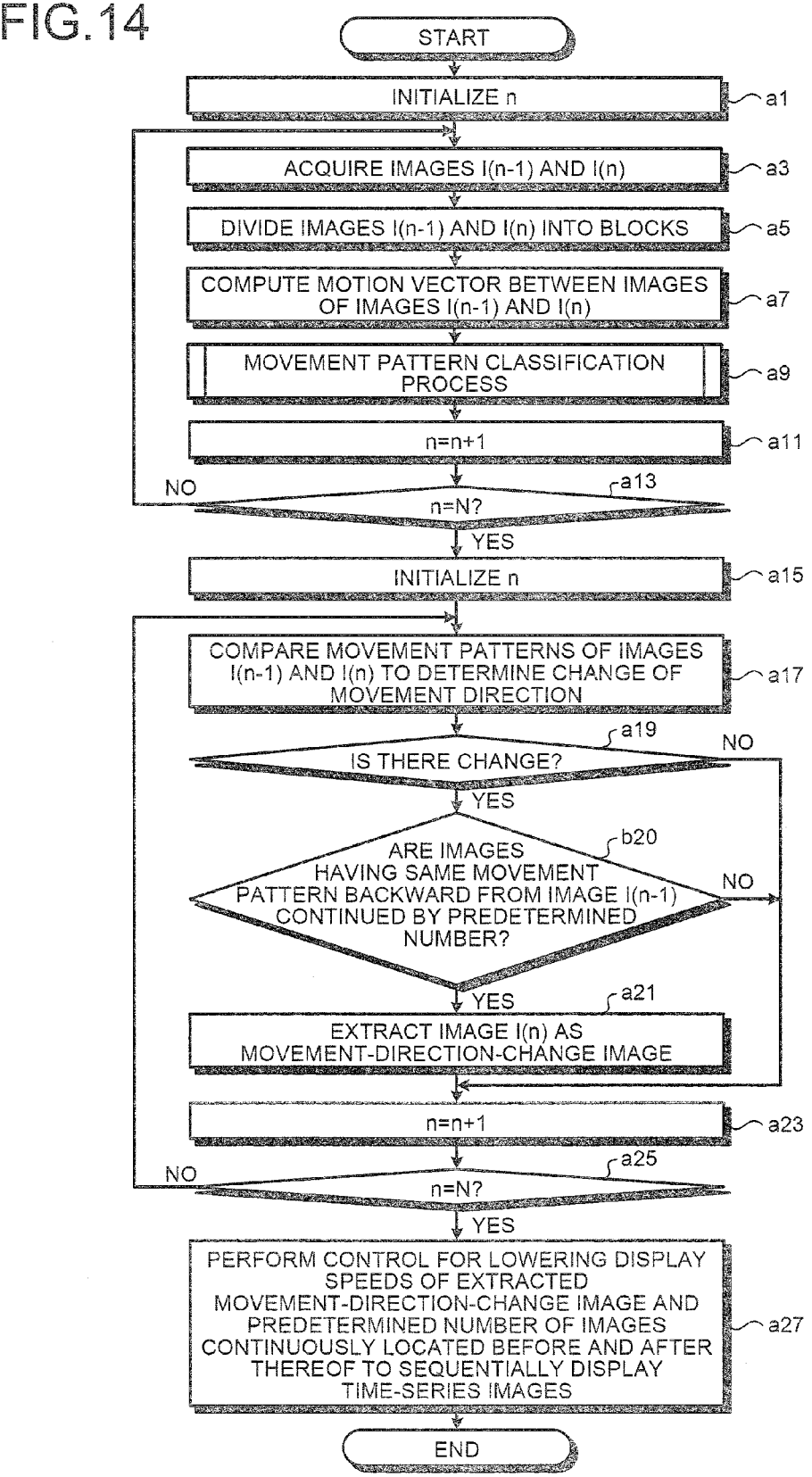
FIG. 14 is a flowchart illustrating a processing procedure of the image processing apparatus according to an alternative example.

In the first embodiment, it has been explained about the case where an image of which the movement direction is changed is extracted as a movement-direction-change image. However, when the movement direction of an image is changed after images having the same movement pattern are continued by a predetermined number, the image processing apparatus may extract an image of which the movement direction is changed as a movement-direction-change image. FIG. 14 is a flowchart illustrating the processing procedure of an image processing apparatus according to the present alternative example. In this case, the same processing steps of FIG. 14 as those illustrated in FIG. 3 in the first embodiment have the same reference numbers.

As illustrated in FIG. 14, in the image processing apparatus of the present alternative example, the movement-direction-change determining unit compares the movement patterns of the images I(n−1) and I(n) to determine the change of a movement direction at Step a17. As a result, when the movement direction is changed (Step a19: Yes), the movement-direction-change determining unit determines whether images having the same movement pattern as that of the image I(n−1) backward from the image I(n−1) are continued by a predetermined number (Step b20). In this case, a value of two or more is previously set as a predetermined number. The value may be a fixed value, or may be a value that can be changed by the operation of a user. When the images are not continued (Step b20: No), the process control moves to Step a23. On the other hand, when the images are continued (Step b20: Yes), the movement-direction-change image extracting unit extracts the image I(n) as a movement-direction-change image after moving the process control to Step a21, and then moves the process control to Step a23.

Figure 15:
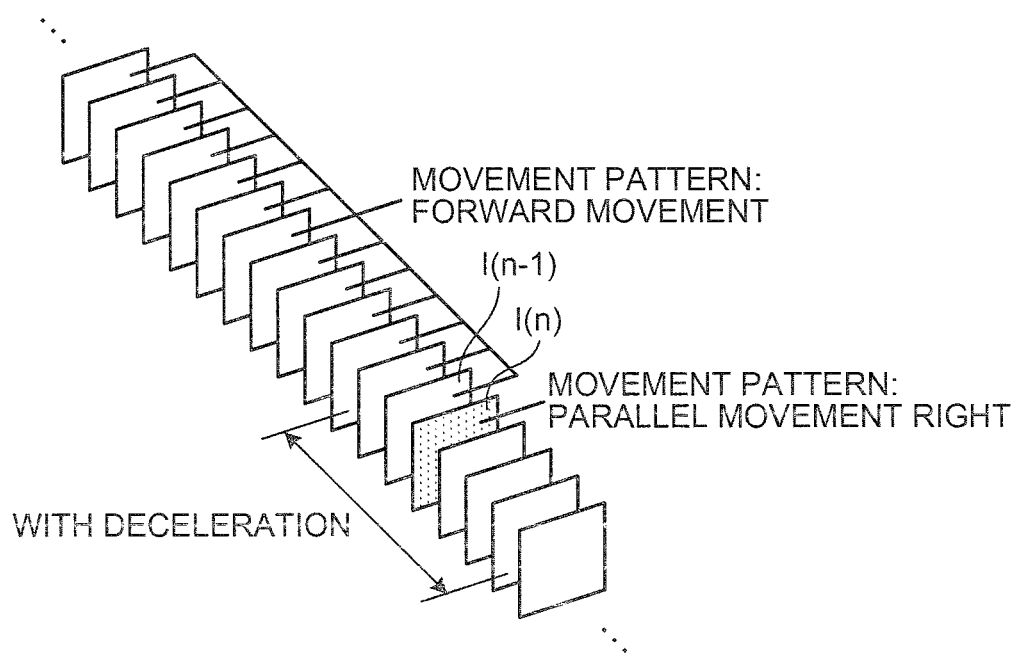
FIG. 15 is a diagram explaining an extraction process of a movement-direction-change image according to the alternative example.

FIG. 15 is a diagram explaining an extraction process of a movement-direction-change image according to the present alternative example, and illustrates time-series images that are continued from the rear side toward the front side of FIG. 15. As illustrated in FIG. 15, after a predetermined number or more images of which the movement patterns are "forward movement" are continued to the image I(n−1), the image I(n) is extracted as a movement-direction-change image when the movement pattern is changed to "parallel movement right" at the image I(n). In this case, the display speeds of the image I(n) and the predetermined number of images continuously located before and after the image I(n) are decelerated. According to the present alternative example, when the movement direction is changed after images having the same movement pattern are continued, the image of which the movement direction is changed can be observed at a slower display speed than that of the other images. Therefore, it is possible to prevent the delay of recognition for the sudden change of the movement direction of an image and the missing of important information caused by the delay of recognition.

Second Embodiment

Figure 16:
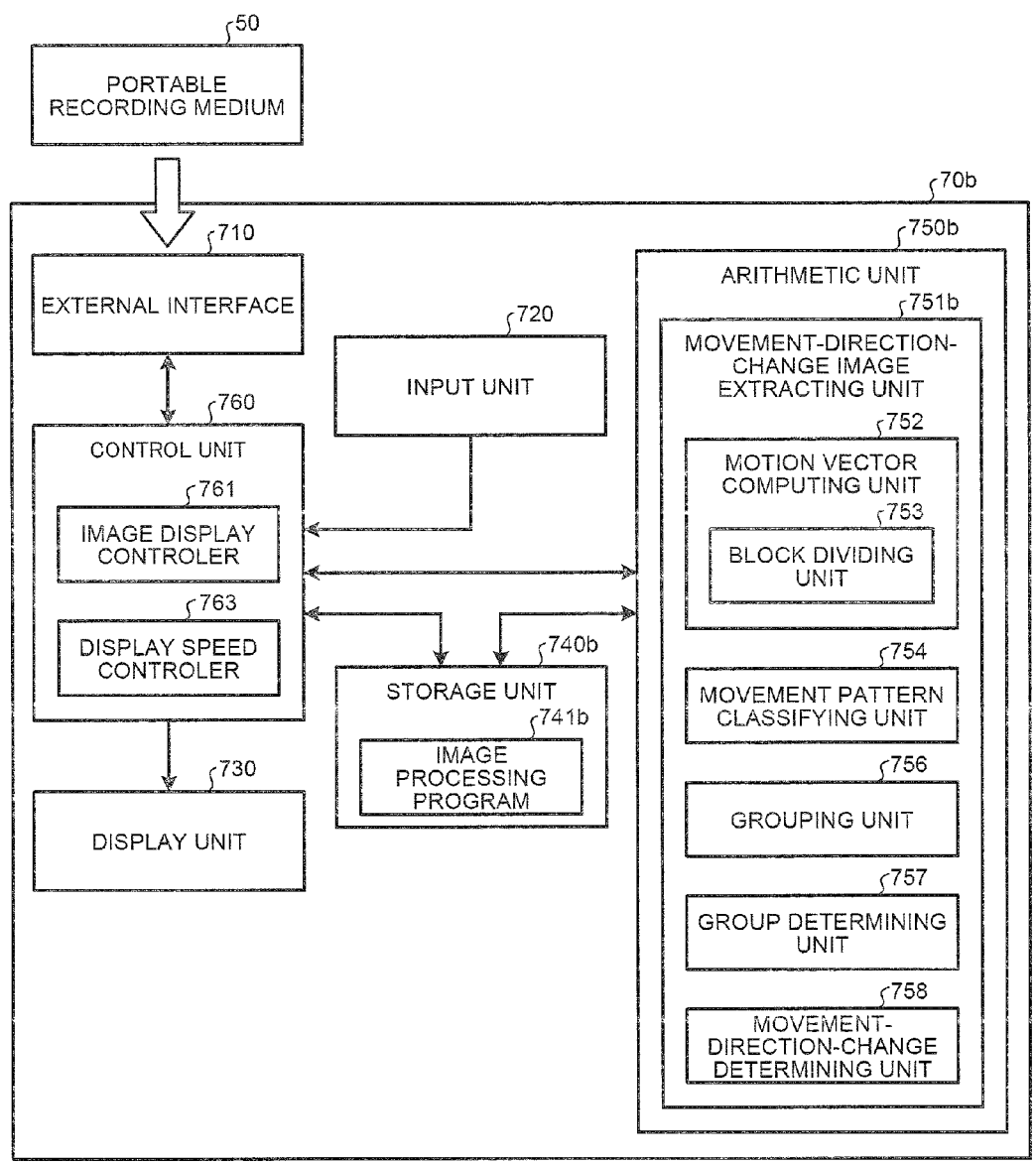
FIG. 16 is a block diagram explaining the functional configuration of an image processing apparatus according to a second embodiment.

Next, it will be explained about a second embodiment. FIG. 16 is a block diagram explaining the functional configuration of an image processing apparatus 70b according to the second embodiment. In this case, the same configuration as that explained in the first embodiment has the same reference number. In the second embodiment, the image processing apparatus 70b includes the external interface 710, the input unit 720, the display unit 730, a storage unit 740b, an arithmetic unit 750b, and the control unit 760 that controls all the operations of the image processing apparatus 70b. The storage unit 740b stores therein an image processing program 741b.

The arithmetic unit 750b includes a movement-direction-change image extracting unit 751b. The movement-direction-change image extracting unit 751b includes the motion vector computing unit 752 that includes the block dividing unit 753, the movement pattern classifying unit 754, a grouping unit 756 that functions as a grouping means, a group determining unit 757 that functions as a group determining means, and a movement-direction-change determining unit 758. The grouping unit 756 groups time-series consecutive images of which the movement patterns are the same. The group determining unit 757 determines whether adjacent groups that are grouped are a group that is configured of images not less than a predetermined number of reference images. In the present embodiment, in adjacent time-series images, the number of pre-reference images that are applied to a forward group and the number of post-reference images that are applied to a backward group are previously set as the number of reference images. The movement-direction-change determining unit 758 determines the change of a movement direction between groups. Then, the movement-direction-change image extracting unit 751b extracts, as a movement-direction-change image, a time-series forehand image in the group of which the movement direction is changed, which is determined by the movement-direction-change determining unit 758.

Figure 17:
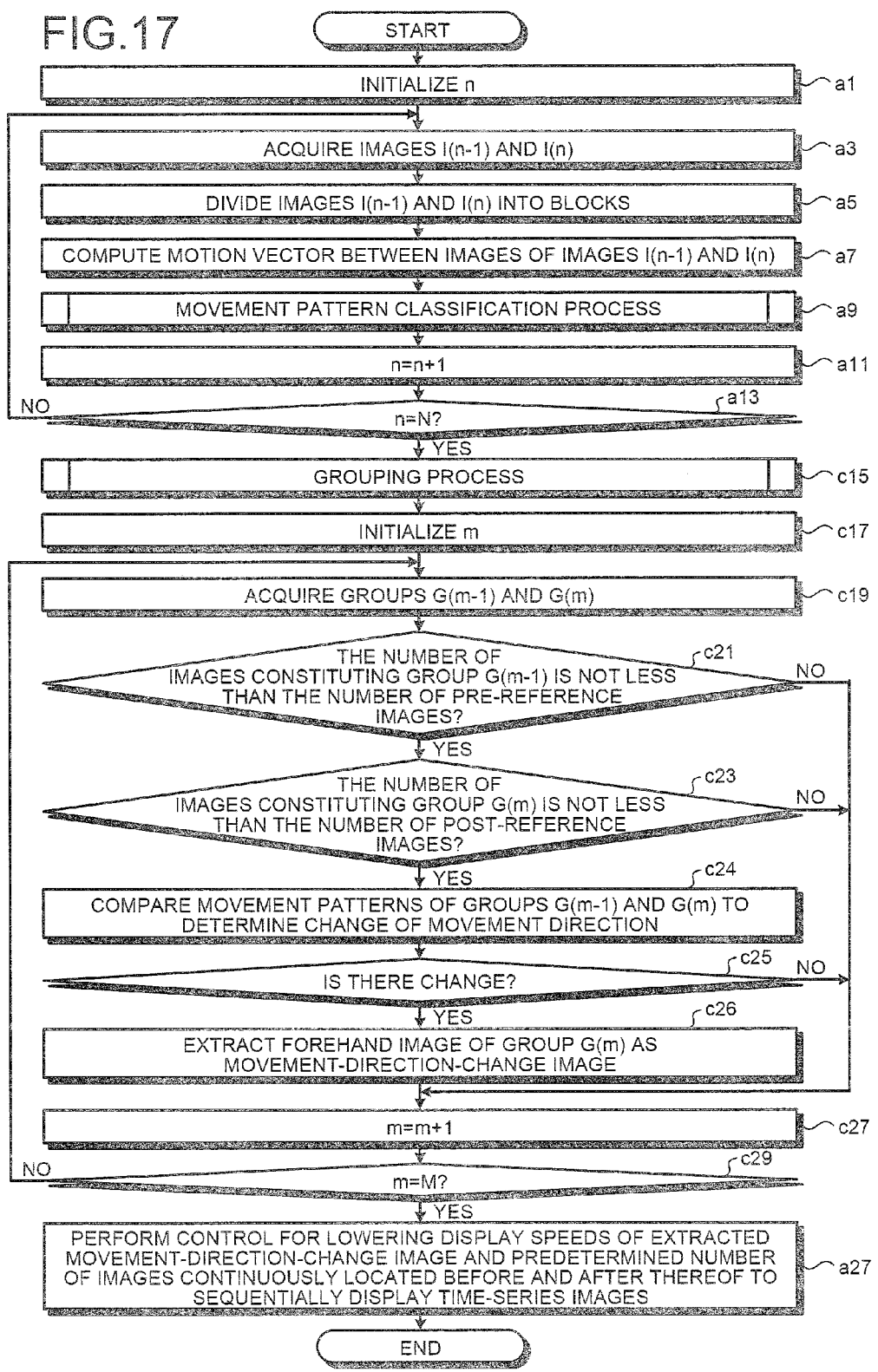
FIG. 17 is a flowchart illustrating a processing procedure performed by the image processing apparatus according to the second embodiment.

FIG. 17 is a flowchart illustrating a processing procedure performed by the image processing apparatus 70b according to the second embodiment. A process explained here is realized by the operations of the units of the image processing apparatus 70b in accordance with the image processing program 741b that is stored in the storage unit 740b. The same processing steps of FIG. 17 as those of FIG. 3 in the first embodiment have the same reference numbers.

Figure 18:
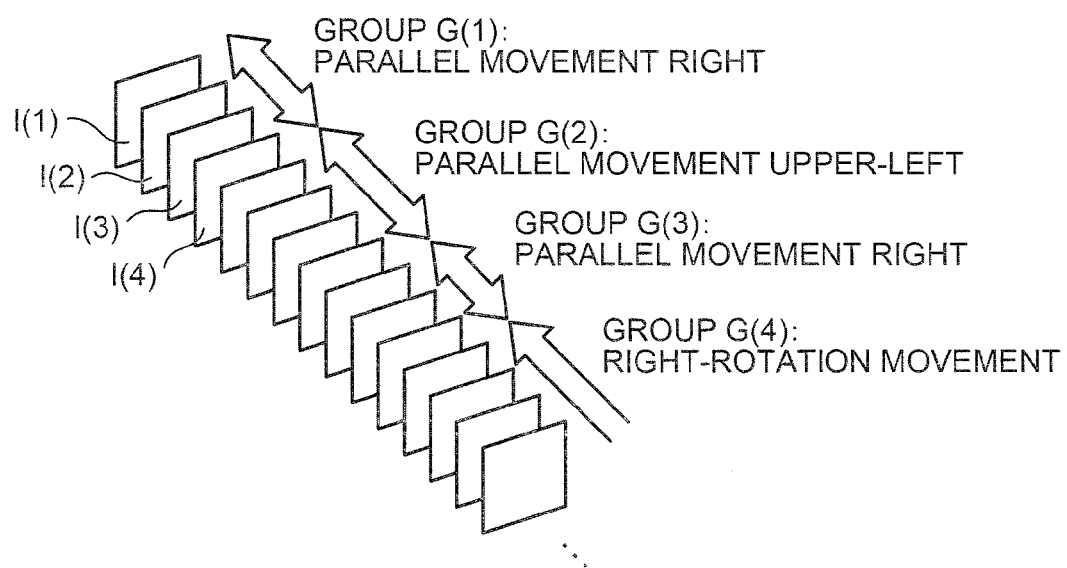
FIG. 18 is a diagram explaining a grouping process.

As illustrated in FIG. 17, in the image processing apparatus 70b according to the second embodiment, at Step a13, when it is determined that n=N (Step a13: Yes), the grouping unit 756 executes a grouping process (Step c15). FIG. 18 is a diagram explaining a grouping process and illustrates time-series images that are continued from the innermost forehand (image number 1) image I(1) of FIG. 18 toward the front side. In the grouping process, time-series consecutive images of which the movement patterns are the same are grouped as an image group. In an example of FIG. 18, images I(1) to I(4) of which the movement patterns are classified into "parallel movement right" are grouped as a group G(1). Next to the group G(1), four images of which the image patterns are classified into "parallel movement upper-left" are grouped as a group G(2). Next to the group G(2), three images of which the image patterns are classified into "parallel movement right" are grouped as a group G(3). Next to the group G(3), images of which the image patterns are classified into "right-rotation movement" are grouped as a group G(4).

Figure 19:
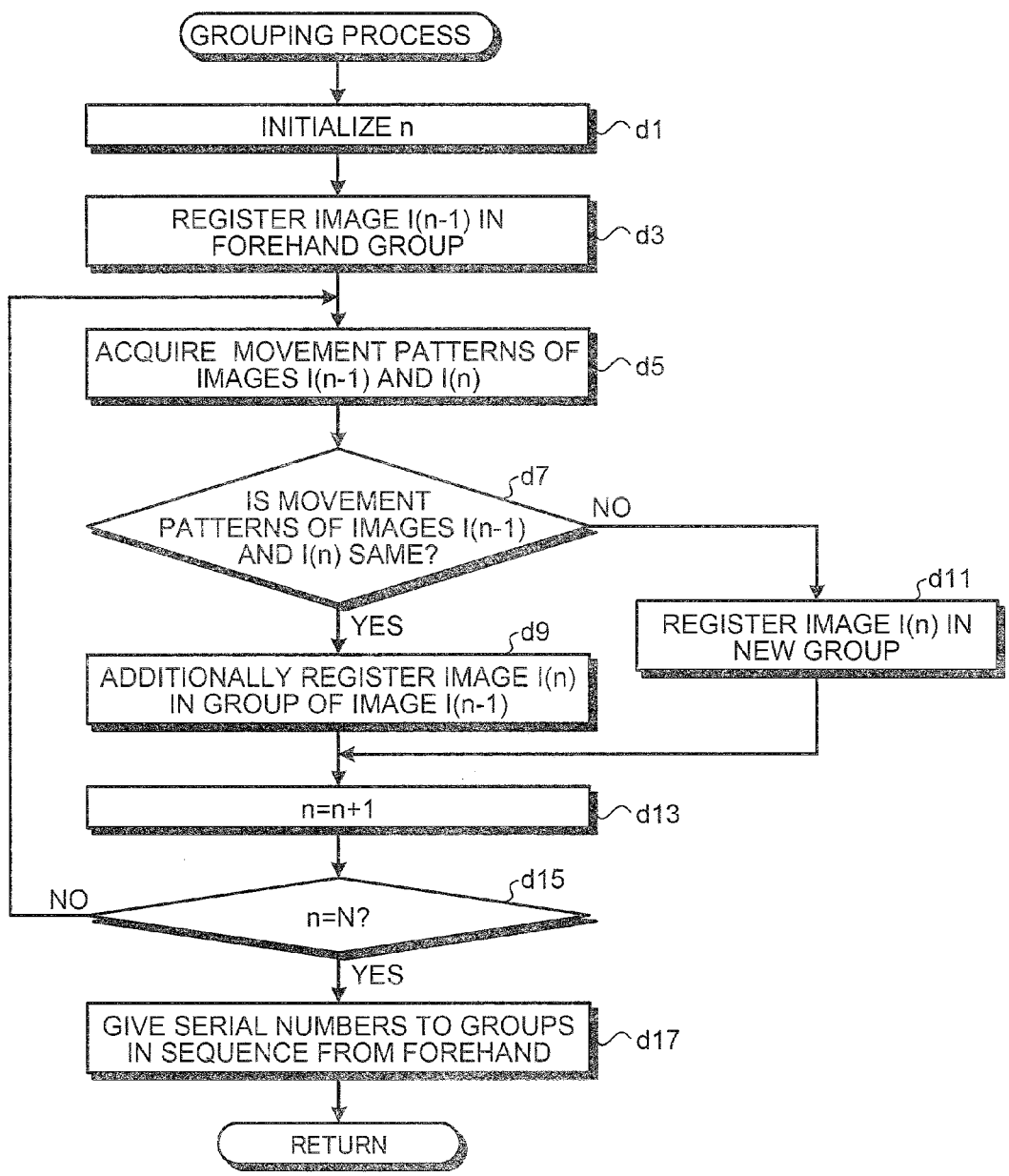
FIG. 19 is a flowchart illustrating the detailed processing procedure of the grouping process.

FIG. 19 is a flowchart illustrating the detailed processing procedure of a grouping process. In the grouping process, the grouping unit 756 first initializes the image number "n" once again (Step d1), and registers the image I(n−1) in a forehand group (Step d3). Next, the grouping unit 756 reads out and acquires the movement patterns of the images I(n−1) and I(n) classified at Step a9 of FIG. 17 from the storage unit 740b (Step d5). Then, the grouping unit 756 compares the acquired movement patterns. When the movement patterns are the same (Step d7: Yes), the grouping unit 756 additionally registers the image I(n) in the group that is registering the image I(n−1) (Step d9). On the other hand, when the movement patterns are different (Step d7: No), the grouping unit 756 newly creates a group to register the image I(n) (Step d11). Then, the grouping unit 756 increments the image number "n" to be n=n+1 (Step d13), and determines the presence or absence of an image that is the next processing target in accordance with whether the value of "n" is identical with the total number "N" of images that constitute time-series images. If it is not n=N (Step d15: No), the process control is returned to Step d5. On the other hand, if it is n=N (Step d15: Yes), the grouping unit 756 gives serial numbers to the groups in sequence from the forehand group (Step d17), and returns the process control to Step c15 of FIG. 17. The data (group information) of each group that is grouped is maintained in the storage unit 740b. Specifically, the image number of the last of a group, the movement patterns (movement patterns of images constituting a group), and the like are stored in association with the serial number given to each group.

Then, as illustrated in FIG. 17, after the grouping process is executed, the group determining unit 757 initializes a group number "m" for identifying a group that is a processing target (Step c17). Then, the group determining unit 757 reads out and acquires the group information of groups G(m−1) and G(m) from the storage unit 740b (Step c19).

Next, the group determining unit 757 determines whether the number of images constituting the group G(m−1) is not less than the number of pre-reference images. The number of images constituting the group G(m−1) is obtained, for example, by subtracting the image number of the last of a group G(m−2) from the image number of the last of the group G(m−1). Then, when it is not less than the number of pre-reference images (Step c21: Yes), the group determining unit 757 determines whether the number of images constituting the group G(m) is not less than the number of post-reference images. The number of images constituting the group G(m) is obtained, for example, by subtracting the image number of the last of the group G(m−1) from the image number of the last of the group G(m). In this case, a value of one or more is previously set to the number of pre-reference images and the number of post-reference images. The number of pre-reference images and the number of post-reference images may be a fixed value, or may be changed by the operation of a user.

Then, when the number of images is not less than the number of post-reference images (Step c23: Yes), the group determining unit 757 compares the movement patterns of the groups G(m−1) and G(m) and determines the change of a movement direction (Step c24). Then, as illustrated in FIG. 17, when the movement direction is not changed (Step c25: No), the process control moves to Step c27. At this time, when the movement patterns of the groups G(m−1) and G(m) are "the other", the process control may move to Step c27 without performing the process of the subsequent Step c26. On the other hand, when the movement direction is changed (Step c25: Yes), the movement-direction-change image extracting unit 751b extracts a time-series forehand image of the group G(m) as a movement-direction-change image (Step c26), and moves the process control to Step c27.

Figure 20:
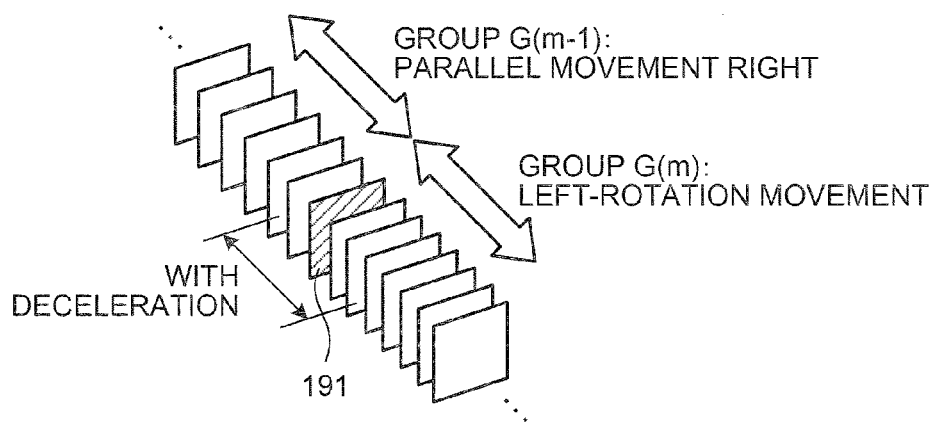
FIG. 20 is a diagram explaining the determination method of the change of a movement direction.
Figure 21:
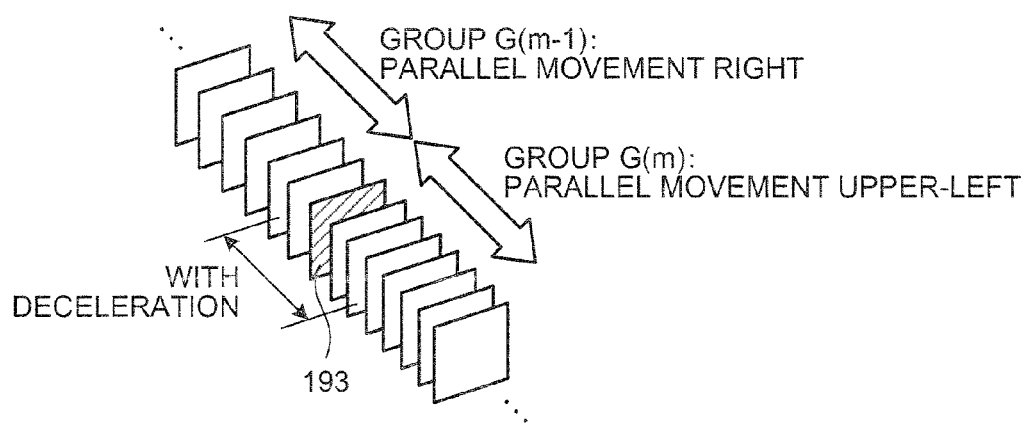
FIG. 21 is a diagram explaining the determination method of the change of a movement direction.
Figure 22:
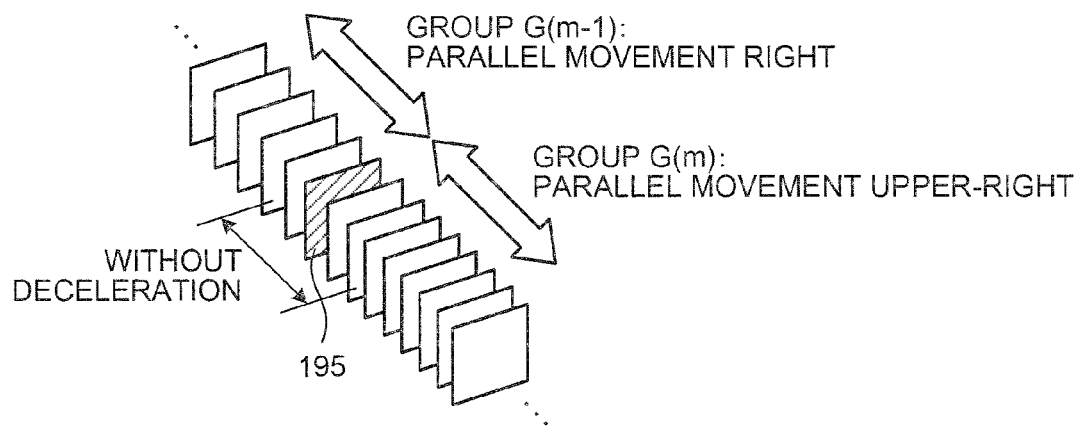
FIG. 22 is a diagram explaining the determination method of the change of a movement direction.

FIGS. 20 to 22 are diagrams explaining the determination method of the change of a movement direction. In the present determination method, it is assumed that "parallel movement", "rotation movement", "forward movement", "reverse movement", and "the other" among movement patterns are parent patterns. Moreover, it is assumed that "parallel movement upper", "parallel movement upper-left", "parallel movement left", "parallel movement lower-left", "parallel movement lower", "parallel movement lower-right", "parallel movement right", and "parallel movement upper-right" are child patterns for the parent pattern "parallel movement". Moreover, it is assumed that "left-rotation movement" and "right-rotation movement" are child patterns for the parent pattern "rotation movement". For example, as illustrated in FIG. 20, when the parent patterns of the movement patterns of the groups G(m−1) and G(m) are different as "parallel movement" and "rotation movement", it is determined that a movement direction is changed. Therefore, when displaying the time-series images, the display speeds of a forehand image 191 and the predetermined number of images, which are continuously located before and after the image 191, in the time-series images of the group G(m) are decelerated. On the other hand, when the parent patterns of the movement patterns of the groups G(m−1) and G(m) are "parallel movement" and the change of the movement pattern is the change of a moving direction, it is determined whether the moving directions of child patterns are similar.

For example, "upper" and "upper-left", "upper-left" and "left", "left" and "lower-left", "lower-left" and "lower", "lower" and "lower-right", "lower-right" and "right", "right" and "upper-right", and "upper-right" and "upper" are previously defined as a similar moving direction. Then, as illustrated in FIG. 21, when the child patterns of the movement patterns of the groups G(m−1) and G(m) are "parallel movement right" and "parallel movement upper-left" and the moving directions are not similar, it is determined that a movement direction is changed. Therefore, when displaying the time-series images, the display speeds of a forehand image 193 and the predetermined number of images, which are continuously located before and after the image 193, in the time-series images of the group G(m) are decelerated. On the contrary, as illustrated in FIG. 22, when the child patterns of the movement patterns of the groups G(m−1) and G(m) are "parallel movement right" and "parallel movement upper-right" and the moving directions are similar, it is determined that a movement direction is not changed. Therefore, when displaying the time-series images, the display speeds of a forehand image 195 and the predetermined number of images, which are continuously located before and after the image 195, in the time-series images of the group G(m) are not decelerated.

Then, the group determining unit 757 increments the group number "m" to be m=m+1 (Step c27), and determines the presence or absence of a group that is the next processing target in accordance with whether the value of "m" is identical with the total number "M" of groups. If it is not m=M (Step c29: No), the process control is returned to Step c19. On the other hand, if it is m=M (Step c29: Yes), the process control moves to Step a27, and the image display controller 761 performs a control for sequentially displaying images constituting the time-series images in time sequence. At this time, the display speed controller 763 performs a control for lowering the display speeds of the movement-direction-change image extracted at Step c26 and the predetermined number of images that are continuously located before and after the movement-direction-change image relatively compared to the display speeds of the other images.

As described above, according to the second embodiment, the same effect as that of the first embodiment can be obtained. Moreover, the image processing apparatus can group time-series consecutive images of which the movement patterns are the same among images constituting time-series images and determine the change of a movement direction in units of group. Then, on condition that the predetermined number of images of which the movement patterns are the same are continuously located before and after the image of which the movement pattern is changed in addition to the change of a movement direction, a movement-direction-change image can be extracted.

In the embodiment, it has been explained about the case where the inside-subject 1 image captured by the capsule endoscope 10 is displayed. However, the present invention is not limited to this. The invention can be similarly applied to the case where time-series images consisting of a plurality of images are sequentially displayed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus for sequentially displaying time-series images, comprising:
    a movement-direction-change image extracting unit that detects a movement between consecutive images constituting the time-series images and extracts an image of the consecutive images in which a movement direction is changed in comparison to a respective movement in a previous image of the consecutive images; and
    a display speed controller that controls display speeds of the image extracted by the movement-direction-change image extracting unit and images adjacent to the image at a level relatively lower than display speeds of other images.

2. The image processing apparatus according to claim 1, wherein the movement-direction-change image extracting unit includes
    a motion vector computing unit that computes a motion vector between the images constituting the time-series images; and
    a movement pattern determining unit that determines a movement pattern based on the motion vector computed by the motion vector computing unit, and
    the movement-direction-change image extracting unit extracts the image of which the movement pattern is changed, which is classified by the movement pattern determining unit.

3. The image processing apparatus according to claim 2, wherein the movement pattern determining unit determines the movement pattern in accordance with a direction of the motion vector computed by the motion vector computing unit.

4. The image processing apparatus according to claim 2, wherein the movement pattern determining unit classifies the movement pattern into any one of parallel movement, rotation movement, forward movement, reverse movement, and the other according to a moving direction.

5. The image processing apparatus according to claim 4, wherein the movement-direction-change image extracting unit does not extract the image of which the movement pattern is changed when the change of the movement pattern is the change of a moving direction that is parallel movement and the changed moving directions are similar.

6. The image processing apparatus according to claim 2, wherein the movement-direction-change image extracting unit extracts the image of which the movement pattern is changed when images having the same movement pattern among the time-series images are continuously located by a predetermined number and then a movement pattern of an image is changed.

7. The image processing apparatus according to claim 6, wherein the movement-direction-change image extracting unit extracts, when images having one movement pattern among the time-series images are continuously located by a predetermined number and then images having a movement pattern different from the one movement pattern are continuously located by a predetermined number, an image of which a movement pattern is changed to the different movement pattern.

8. The image processing apparatus according to claim 7, wherein the movement-direction-change image extracting unit includes
    a grouping unit that groups time-series consecutive images of which movement patterns are the same; and
    a group determining unit that determines whether adjacent groups grouped by the grouping unit are a group that consists of images not less than a number of reference images that is preset, and
    the movement-direction-change image extracting unit extracts a time-series forehand image of the group of which a movement direction is changed, on the basis of movement patterns of the adjacent groups of which each consists of images not less than the number of reference images, which is determined by the group determining unit.

9. The image processing apparatus according to claim 8, wherein
a number of pre-reference images that is applied to a time-series forward group and a number of post-reference images that is applied to a time-series backward group are previously set as the number of reference images, and
the group determining unit determines, among the adjacent groups, whether the time-series forward group is a group that consists of images not less than the number of pre-reference images and determines whether the time-series backward group is a group that consists of images not less than the number of post-reference images.

10. The image processing apparatus according to claim 1, wherein the display speed controller lowers display speeds of a predetermined number of images, which are continuously located before and after the image extracted by the movement-direction-change image extracting unit as the adjacent images, relatively compared to the display speeds of the other images.

11. A computer readable recording device including programmed instructions, wherein the instructions, when executed by a computer that includes a display unit for sequentially displaying time-series images, cause the computer to execute:
detecting a movement between consecutive images constituting the time-series images;
extracting an image of the consecutive images in which a movement direction is changed in comparison to a respective movement in a previous image of the consecutive images; and
controlling display speeds of the extracted image and images adjacent to the extracted image at a level relatively lower than display speeds of other images.

* * * * *